(12) United States Patent
Hisada

(10) Patent No.: US 6,482,196 B1
(45) Date of Patent: Nov. 19, 2002

(54) DISPOSABLE UNDERGARMENT

(75) Inventor: Kenichi Hisada, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 09/399,739

(22) Filed: Sep. 20, 1999

Related U.S. Application Data

(63) Continuation-in-part of application No. 08/979,324, filed on Nov. 26, 1997, now abandoned, which is a continuation of application No. 08/632,827, filed on Apr. 16, 1996, now Pat. No. 5,746,731.

(30) Foreign Application Priority Data

Apr. 26, 1995 (JP) .............................................. 7-102279

(51) Int. Cl.[7] .......................... A61F 13/18; A41C 1/00; A41C 1/08
(52) U.S. Cl. .............................. 604/385.3; 604/385.27; 604/392; 604/396; 450/154; 450/155
(58) Field of Search ............... 604/385.19, 385.01–402; 2/71–73, 76, 78.3, 109–112, 212–213, 220–222, 406–409, 229, 236, 237, 311, 312, 49; 450/154–155

(56) References Cited

U.S. PATENT DOCUMENTS 1,410,870 A   3/1922   Atkinson
1,458,082 A   6/1923   Stein
1,491,528 A   4/1924   Guinzburg
5,449,353 A   9/1995   Watanabe et al.

FOREIGN PATENT DOCUMENTS

| FR | 1 104 352 | 11/1955 |
| JP | 2-33202 | 3/1990 |
| JP | 2-106406 | 8/1990 |
| JP | 3-33201 | 2/1991 |
| JP | 3-82467 | 4/1991 |
| JP | 4-289201 | 10/1992 |

Primary Examiner—Glenn K. Dawson
Assistant Examiner—Karin M. Reichle
(74) Attorney, Agent, or Firm—Lowe Hauptman Gilman & Bener, LLP

(57) ABSTRACT

A disposable undergarment has an integrated belly protector and pants. The belly protector has a front body and a rear body joined together to form a tubular configuration having upper and lower openings. A first elastic member is secured along the upper opening. Second and third elastic members are secured to the front body between the first elastic member and the lower opening so as to extend with a transversely symmetric arrangement and to curve convexly toward the upper and lower openings, respectively. The pants have a front body and a rear body joined together to define a waist-opening and a pair of leg-openings. The waist-opening of the pants is seamlessly connected to the lower opening of the belly protector, and a fourth elastic member is secured along the waist opening.

15 Claims, 4 Drawing Sheets

DISPOSABLE UNDERGARMENT

The present application is a continuation-in-part of U.S. application Ser. No. 08/979,324, filed Nov. 26, 1997, now abandoned, which is a continuation of U.S. application Ser. No. 08/632,827, filed Apr. 16, 1996, now U.S. Pat. No. 5,746,731.

BACKGROUND OF THE INVENTION

The present invention relates to a disposable undergarment such as a belly protector and a combination with such a belly protector.

A belly protector of tubular configuration formed of an elastic sheet material such as a rib stitched fabric is generally known in the art. A belly protector with pants is also known, for example, in Japanese Laid-Open Utility Model Application Nos. Hei 2-33202 and Hei 2-106406.

However, the known belly protectors have a uniform elasticity and often exert an unacceptable pressure on the wearer's belly, particularly when the belly is bulging, sometimes causing an uncomfortable choking feeling for the wearer.

Accordingly, it is a principal object of the invention to provide a disposable undergarment, particularly a belly protector having elastic members surrounding the prominence of the wearer's belly to solve the above mentioned problem.

SUMMARY OF THE INVENTION

In one aspect of the present invention, there is provided a disposable undergarment comprising an integrated belly protector and pants. The belly protector comprises: a front body and a rear body joined together along transversely opposite side edges thereof so as to form a tubular configuration having upper and lower openings; a first elastic member secured in an elastically contractible condition along the upper opening; and second and third elastic members secured in an elastically contractible condition to at least the front body between the first elastic member and the lower opening so as to extend between the transversely opposite side edges of the front body with a transversely symmetric arrangement and to only curve convexly toward the upper and lower openings, respectively. The pants comprise: a front body and a rear body joined together along transversely opposite side edges thereof so as to define a waist-opening and a pair of leg-openings, the waist-opening of the pants being seamlessly connected to the lower opening of the belly protector; and a fourth elastic member secured in an elastically contractible condition along the waist opening.

In another aspect of the present invention, there is provided a disposable undergarment comprising an integrated belly protector and pants. The belly protector comprises: a front body and a rear body joined together along transversely opposite side edges thereof so as to form a tubular configuration having upper and lower openings; a first elastic member secured in an elastically contractible condition along the upper opening; and second and third elastic members secured in an elastically contractible condition to at least the front body between the first elastic member and the lower opening so as to extend between the transversely opposite side edges of the front body with a transversely symmetric arrangement and to only curve convexly toward the upper and lower openings, respectively. The pants comprise: a front body and a rear body joined together along transversely opposite side edges thereof so as to define a waist-opening and a pair of leg-openings, the waist-opening of the pants being seamlessly connected to the lower opening of the belly protector.

In even another aspect of the present invention, there is provided a disposable undergarment comprising an integrated belly protector and pants. The belly protector comprises: a front body and a rear body joined together along transversely opposite side edges thereof so as to form a tubular configuration having upper and lower openings; a first elastic member secured in an elastically contractible condition along the upper opening; and a second elastic member secured in an elastically contractible condition to at least the front body between the first elastic member and the lower opening so as to extend between the transversely opposite side edges of the front body with a transversely symmetric arrangement and to only curve convexly toward the upper opening. The pants comprise: a front body and a rear body joined together along transversely opposite side edges thereof so as to define a waist-opening and a pair of leg-openings, the waist-opening of the pants being seamlessly connected to the lower opening of said belly protector; and an elastic member secured in an elastically contractible condition along the waist opening.

The inventive undergarment fits well around the wearer's waist under the effect of the first elastic member. The belly protector, particularly its front body contacts the wearer's belly above and below its prominence under the effect of elastic members. In this way, the belly protector fits well around the wearer's waist and belly while a direct pressure exerted on the prominence of the wearer's belly is reliably avoided.

DETAILED DESCRIPTION OF THE PREFERRED EMBODIMENT

Figure 1:
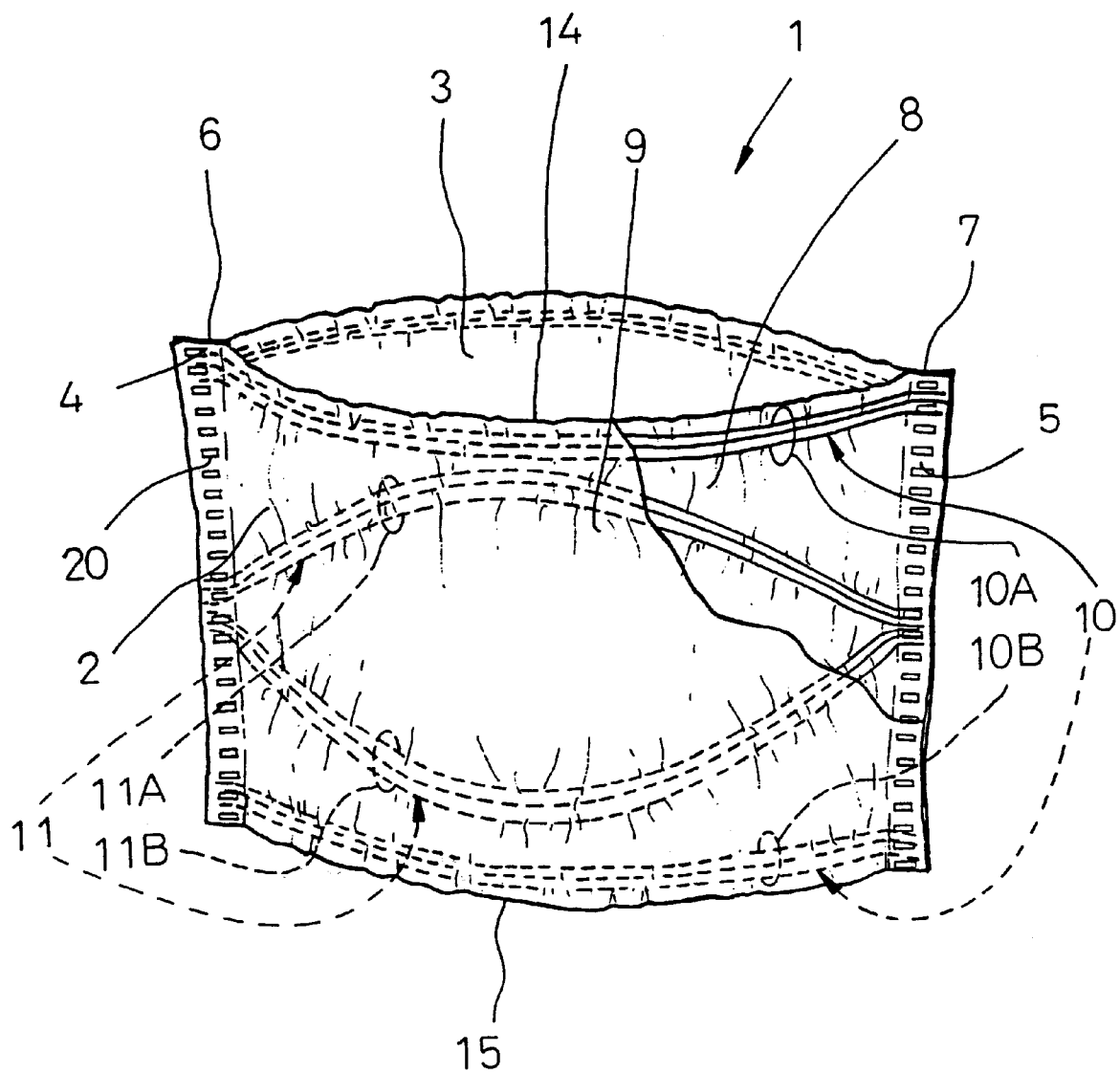
FIG. 1 is a perspective view showing a disposable undergarment as a belly protector of the invention as partially broken away.

Referring to FIG. 1, a belly protector 1 comprises a rectangular front body member 2 and a rectangular rear body member 3. These front and rear members 2, 3 are joined together along transversely opposite edges 4, 5, 6, 7, in an overlapping relation to form a tubular configuration. Since the front and rear bodies 2, 3 are substantially identical with each other with respect to their constructions, shapes and sizes, these front and rear bodies 2, 3 will be described below only with respect to the front body.

The front body 2 comprises inner and outer sheets 8, 9 both formed of a non-woven fabric containing thermoplastic synthetic fabrics of 20 or higher % by weight, and first and second elastic members 10, 11 disposed between the inner and outer sheets 8, 9. Each of the first and second elastic members 10, 11 includes a desired number of individual elastic elements or threads. It is to be understood that the plurality of elastic elements comprising each of elastic members 10, 11 can be substituted with a single elastic element or thread, or with a single elastic band. The inner and outer sheets 8, 9 are bonded to each other by heating the thermoplastic synthetic fibers at desired locations or by means of hot melt adhesives applied to the desired locations. The first and second elastic members 10, 11 are secured in an elastically contractible condition to one or both of the inner and outer sheets 8, 9. The first elastic member 10 comprises an upper elastic member 10A extending along an upper opening 14 and a lower elastic member 10B extending along a lower opening 15 of the front body 2. The second elastic member 11 comprises an upper elastic member 11A only curved convexly toward the upper opening 14 and a lower elastic member 11B only curved convexly toward the lower opening 15. The upper and lower elastic members 11A, 11B respectively extend between the side edges 4, 5, with a transversely symmetric arrangement and preferably terminate substantially at middle points of the side edges 4, 5, as viewed in a vertical direction. The upper and lower elastic members 11A, 11B are spaced from each other by the maximum distance midway between the side edges 4, 5. Each of the first and second elastic members 10, 11 arranged in this manner may have a desired elasticity and elongation percentage and the individual elastic elements of the elastic members may be arranged parallel to each other in suitably spaced condition. Alternatively, the respective elastic members may have their elongation percentages varying transversely of the front body 2 and/or the rear body 3.

The front and rear bodies 2, 3 are joined by heating the thermoplastic synthetic fibers contained in the non-woven fabric at bonding spots 20 intermittently arranged in a vertical direction along the respective side edges 4, 5, 6, 7. The front and rear bodies 2, 3 may be integrated by means of adhesive instead of the heating.

The belly protector 1 constructed as described above is intended to be used so that the transversely middle area of the front body 2 at which the upper and lower elastic members 11A, 11B are spaced from each other by the maximum distance lies on the prominence of the wearer's belly. A direct pressure exerted on the prominence can be thereby alleviated or avoided. For the rear body 3, the elasticity of the upper and lower elastic members arranged on the rear body 3 may be selected to be different from those arranged on the front body 2 or a layout thereof may be selected to be different from the layout thereof of the front body 2 and thereby these elastic members may be eliminated partially or entirely from the rear body.

Figure 2A:
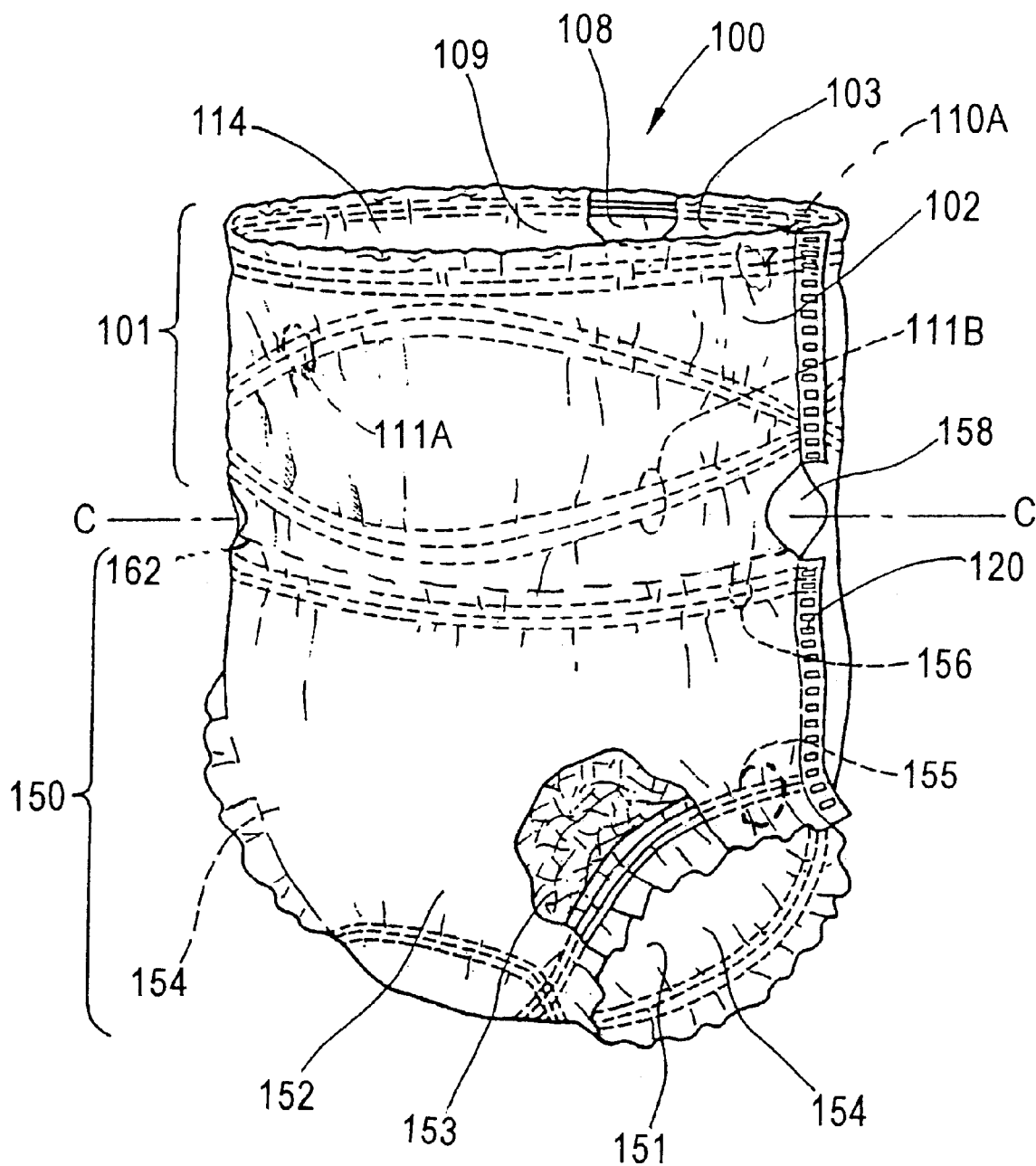
FIG. 2A is a perspective view showing a first arrangement of another disposable undergarment of the invention comprising an integrated belly protector and pants as partially broken away.

Referring to FIG. 2A, there is illustrated a first arrangement of another embodiment of the invention, which is a belly protector 100 integrated with a disposable diaper of pants type or a disposable training pants (both referred to hereinafter simply as pants).

The belly protector 100 comprises a belly protector section 101 and a pants section 150 formed of a continuous, non-woven fabric divided by an imaginary boundary line C—C. The belly protector section 101 defined above the line C—C in FIG. 2A is identical to belly protector 1 illustrated in FIG. 1, except that lower elastic member 10B is eliminated and reference numerals designating like elements are increased by 100. Specifically, belly protector section 101 includes an upper elastic member 110A extending along an upper opening 114 of belly protector section 101. Belly protector section 101 also includes an upper elastic member 111A only curved convexly toward upper elastic member 110A of belly protector section 101, and a lower elastic member 111B only curved convexly toward the pants section 150 defined below imaginary boundary line C—C, as depicted in FIG. 2A.

The pants section 150 defined below the line C—C has substantially the same configuration as those disclosed in Japanese Laid-Open Patent Application Nos. Hei 3-33201 and Hei-82467, which are incorporated herein by reference.

The pants section 150 comprises a liquid-permeable top sheet 151, a liquid-impermeable backsheet 152 and a liquid-absorbent core 153 disposed between these sheets 151, 152 and has a pair of leg-openings 154 defined at transversely opposite sides of the pants section 150. Around these leg-openings 154 and a portion corresponding to a waist-opening of the pants, there are provided an elastic member 155 and an elastic member 156, respectively, which are secured in an elastically contractible condition to one or both of the topsheet and backsheet 151, 152 on its or their inner surface(s). The waist opening of the pants is seamlessly connected to the lower opening of the belly protector section. Transversely opposite edges of the pants section 150 are provided with joining spots 120 formed in the same manner as in the case of the belly protector 1. The top and backsheets 151, 152 extend upward beyond the line C—C so as to form respective inner and outer sheets 108, 109 defining the front and rear bodies 102, 103 of the belly protector section 101. Adjacent the line C—C dividing the belly protector section 101 and the pants section 150, the core 153 is not present; core 153 extends up to but not beyond dashed line 162. The transversely opposite edges of sections 101, 150 may be formed, in the vicinity of line C—C, with cutouts 158, if desired, to improve air-permeability of the belly protector 100 and to thereby avoid a stuffiness due to wearing of the diaper.

In certain circumstances, such as when an infant wearing integrated undergarment 100 is experiencing abdominal discomfort, further reducing the pressure exerted on the abdomen of an infant wearing integrated undergarment 100 is advantageous. Accordingly, the present invention provides alternative arrangements of the integrated undergarment embodiment, described below with reference to FIGS. 2B and 2C, wherein such pressure applied to the abdomen of the infant is further reduced.

Figure 2B:
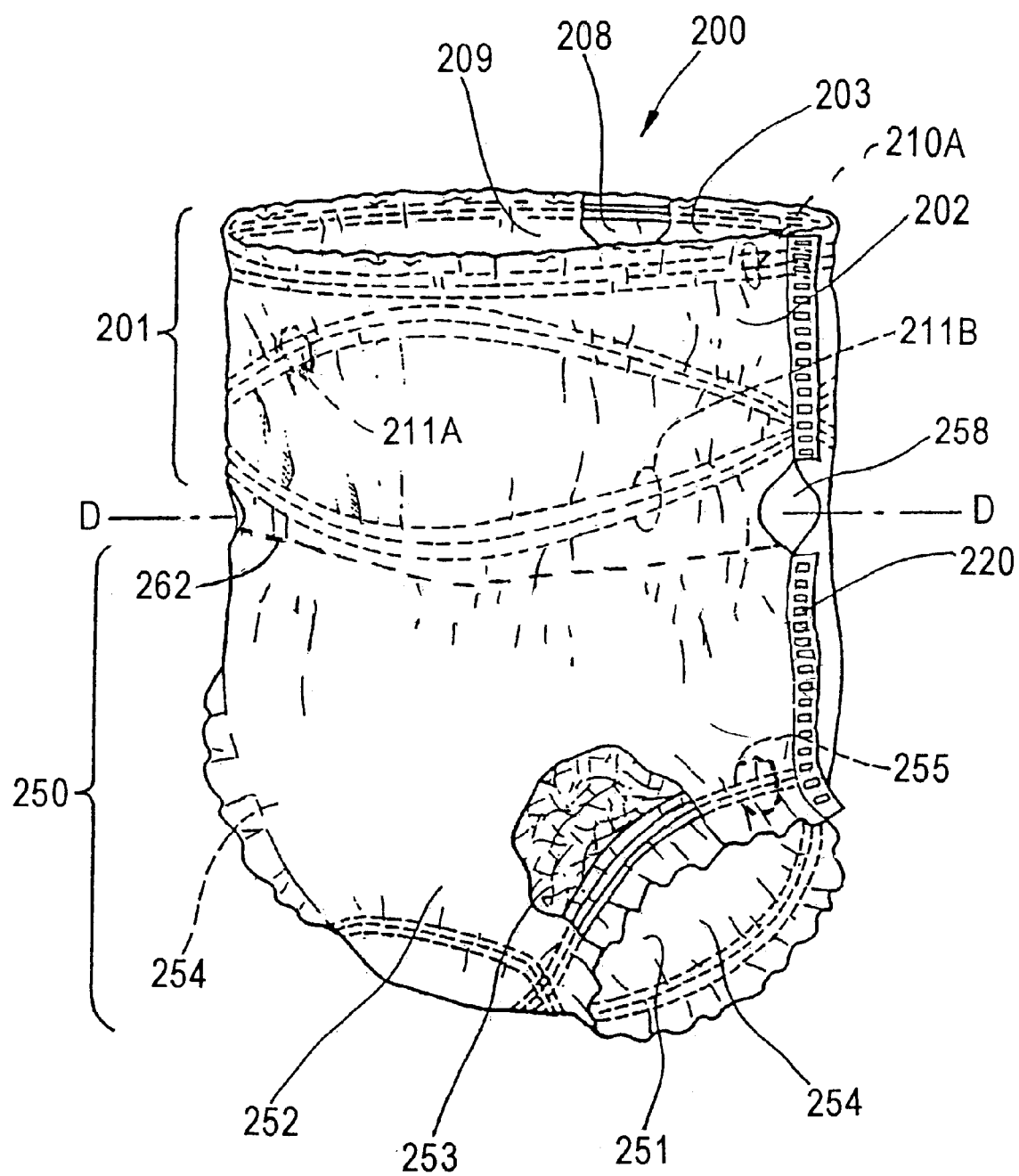
FIG. 2B is a perspective view showing a second arrangement of another disposable undergarment of the invention comprising an integrated belly protector and pants as partially broken away.

With reference to FIG. 2B, there is illustrated a second arrangement of the integrated embodiment, which is a belly protector 200 integrated with pants. The belly protector 200 comprises belly protector section 201 (which is identical to belly protector section 101 of FIG. 2A, except that reference numerals designating like elements are increased by 100) integrated with a pants section 250. The pants section 250 is identical to pants section 150 in FIG. 2A, except that elastic member 156 is eliminated and reference numerals designating like elements are increased by 100. An imaginary section line D—D in FIG. 2B corresponds to imaginary section line C—C in FIG. 2A.

Figure 2C:
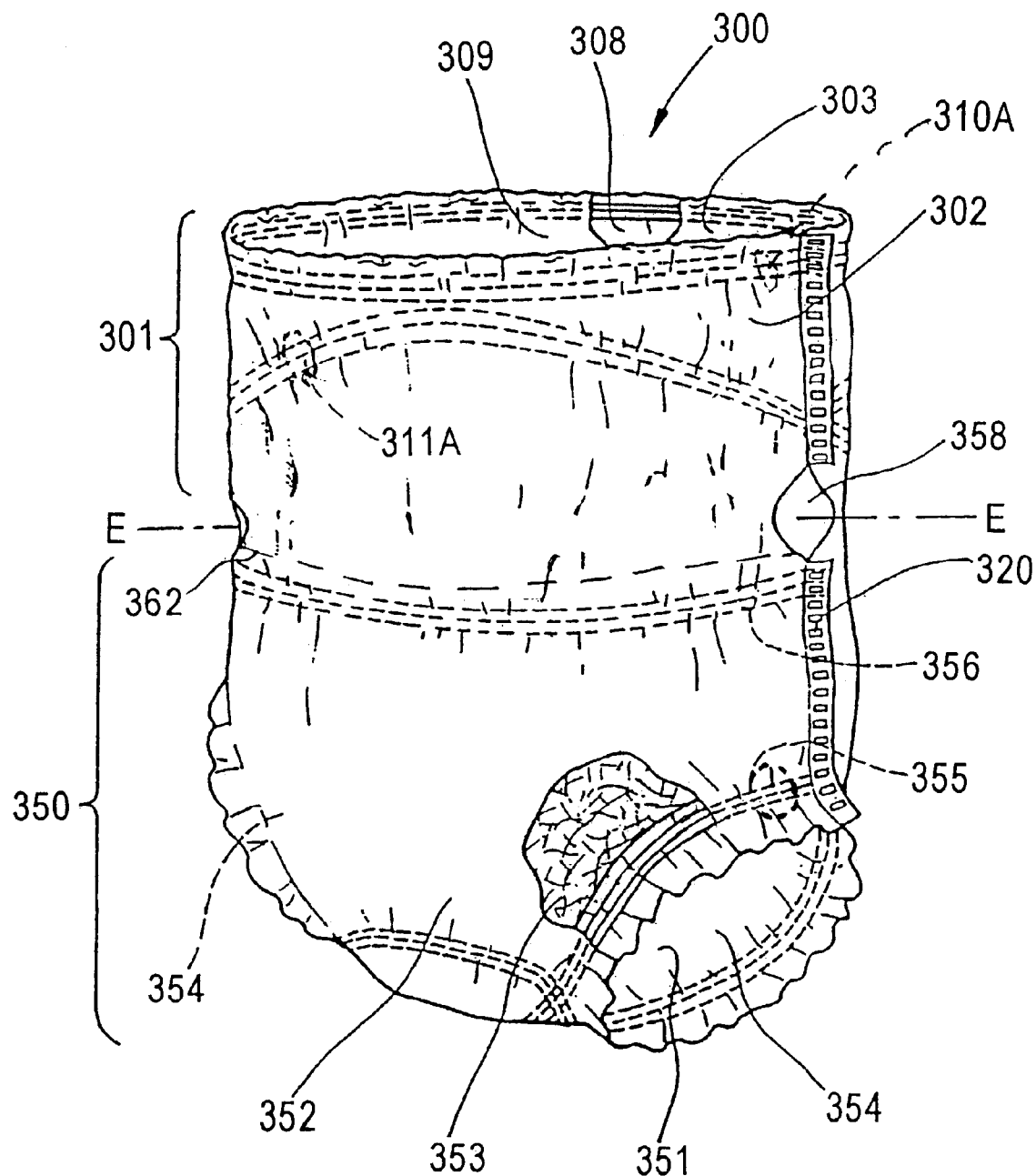
FIG. 2C is a perspective view showing a third arrangement of another disposable undergarment comprising an integrated belly protector and pants as partially broken away.

With reference to FIG. 2C, there is illustrated a third arrangement of the integrated embodiment, which is a belly protector 300 integrated with pants. The belly protector 300 comprises a belly protector section 301 integrated with a pants section 350 (which is identical to pants section 150 of FIG. 2A, except that reference numerals designating like elements are increased by 200). Belly protector section 301 is identical to belly-protector section 101 of FIG. 2A, except that curved, lower elastic member 111B is eliminated, and reference numerals designating like elements are increased by 200. In other words, belly protector section 301, defined above an imaginary section line E—E, is identical to belly protector 1 illustrated in FIG. 1, except that both lower elastic member 10B and lower elastic member 11B are eliminated. The elimination of elastic members 156 and 111B respectively in the second and third arrangements of the belly protectors 200 and 300, as described above, reduces pressure on the abdomen of an infant wearing belly protectors 200 and 300.

It is also possible to make the boundary portion between the belly protector section (e.g., 101) and the pants section (e.g., 150) in any of the integrated embodiments, water-repellent or water-proof in order to prevent the discharged body fluids from spreading into the belly protector section 101.

The inventive belly protectors 100, 200 and 300 integrated with the pants in this unique manner can be put on a baby without being bulky around the waist, which is usually inevitable when a separate diaper and belly protector are put on a baby, allowing for free movement of the baby's body. With the inventive belly protectors 100, 200 and 300, in addition, a direct pressure exerted on the prominence of a potbelly characterizing the babies can be avoided. It should be understood that the pants section 150, 250 and 350 may be replaced by the conventional training pants.

The belly protector of the invention allows direct pressure exerted on the prominence of the wearer's belly to be alleviated or avoided when it is worn, because the front body thereof, in one embodiment, is provided along its upper and lower openings with the first elastic members and between these first elastic members with a pair of the second elastic members only curved convexly toward the upper and lower openings, respectively, so that the area of the front body at which this pair of second elastic members is spaced from each other lies on the prominence of the wearer's belly.

An integrated embodiment of the belly protector of the present invention includes a belly protector section integrated with a pants section. In a first arrangement of the integrated embodiment, the belly protector section includes a first elastic member along the upper opening of the belly protector section, and upper and lower second elastic members only curved convexly toward the upper and lower openings of the belly protector section, respectively. The pants section includes an elastic member around a waist opening of the pants section.

A second arrangement of the integrated embodiment is similar to the first arrangement, except that the elastic member around the waist opening of the pants section is eliminated to reduce pressure exerted on the prominence of the wearer's belly.

A third arrangement of the integrated embodiment is similar to the first arrangement, except that the lower second elastic member of the belly protector section is eliminated to reduce pressure exerted on the prominence of the wearer's belly. In this manner, a level of comfort associated with the wearing of the belly protector can be improved.

What is claimed is:

1. A disposable undergarment comprising a belly protector and pants;

said belly protector comprising:
   a front body and a rear body joined together along transversely opposite side edges thereof so as to form a tubular configuration having upper and lower openings;
   a first elastic member secured in an elastically contractible condition along said upper opening; and
   second and third elastic members secured in an elastically contractible condition to at least said front body between said first elastic member and said lower opening so as to extend between the transversely opposite side edges of said front body with a transversely symmetric arrangement and to only curve convexly toward said upper and lower openings, respectively; and said pants comprising:
   a front body and a rear body joined together along transversely opposite side edges thereof so as to define a waist-opening and a pair of leg-openings, said waist-opening of said pants being seamlessly connected to said lower opening of said belly protector; and
   a fourth elastic member secured in an elastically contractible condition along said waist opening.

2. The disposable undergarment of claim 1, wherein said belly protector and said pants are formed of a continuous common nonwoven fabric.

3. The disposable undergarment of claim 1, wherein
   said waist-opening of said pants is seamlessly connected to said lower opening of said belly protector along an imaginary boundary line; and
   portions of said belly protector and said pants, which are defined between said third and fourth elastic members and located in a vicinity of the imaginary boundary line, are formed at transversely opposite sides thereof with cutouts for air-permeability.

4. The disposable undergarment of claim 1, wherein each said front body and said rear body of said pants comprise a liquid-permeable topsheet, a backsheet and a liquid-absorbent core disposed therebetween.

5. The disposable undergarment of claim 4, wherein
   said waist-opening of said pants is seamlessly connected to said lower opening of said belly protector along an imaginary boundary line; and
   said-liquid absorbent core does not extend beyond the imaginary boundary line and stops at a distance therefrom.

6. A disposable undergarment comprising a belly protector and pants;

said belly protector comprising:
   a front body and a rear body joined together along transversely opposite side edges thereof so as to form a tubular configuration having upper and lower openings;
   a first elastic member secured in an elastically contractible condition along said upper opening; and
   second and third elastic members secured in an elastically contractible condition to at least said front body between said first elastic member and said lower opening so as to extend between the transversely opposite side edges of said front body with a transversely symmetric arrangement and to only curve convexly toward said upper and lower openings, respectively; and said pants comprising:
   a front body and a rear body joined together along transversely opposite side edges thereof so as to define a waist-opening and a pair of leg-openings, said waist-opening of said pants being seamlessly connected to said lower opening of said belly protector.

7. The disposable undergarment of claim 6, wherein said belly protector and said pants are formed of a continuous common nonwoven fabric.

8. The disposable undergarment of claim 6, wherein said waist-opening of said pants is seamless connected to said lower opening of said belly protector along an imaginary boundary line; and portions of said belly protector and said pants, which are located in a vicinity of the imaginary boundary line and below said third elastic member, are formed at transversely opposite sides thereof with cutouts for air-permeability.

9. The disposable undergarment of claim 6, wherein each said front body and said rear body of said pants comprise a liquid-permeable topsheet, a backsheet and a liquid-absorbent core disposed therebetween.

10. The disposable undergarment of claim 9, wherein said waist-opening of said pants is seamlessly connected to said lower opening of said belly protector along an imaginary boundary line; and said-liquid absorbent core does not extend beyond the imaginary boundary line and stops at a distance therefrom.

11. A disposable undergarment comprising a belly protector and pants;

said belly protector comprising:
 a front body and a rear body joined together along transversely opposite side edges thereof so as to form a tubular configuration having upper and lower openings;
 a first elastic member secured in an elastically contractible condition along said upper opening; and
 a second elastic member secured in an elastically contractible condition to at least said front body between said first elastic member and said lower opening so as to extend between the transversely opposite side edges of said front body with a transversely symmetric arrangement and to only curve convexly toward said upper opening; and said pants comprising:
 a front body and a rear body joined together along transversely opposite side edges thereof so as to define a waist-opening and a pair of leg-openings, said waist-opening of said pants being seamlessly connected to said lower opening of said belly protector; and
 an elastic member secured in an elastically contractible condition along said waist opening.

12. The disposable undergarment of claim 11, wherein said belly protector and said pants are formed of a continuous common nonwoven fabric.

13. The disposable undergarment of claim 11, wherein said waist-opening of said pants is seamlessly connected to said lower opening of said belly protector along an imaginary boundary line; and portions of said belly protector and said pants, which are located in a vicinity of the imaginary boundary line and above said elastic member of said pants, are formed at transversely opposite sides thereof with cutouts for air-permeability.

14. The disposable undergarment of claim 11, wherein each said front body and said rear body of said pants comprise a liquid-permeable topsheet, a backsheet and a liquid-absorbent core disposed therebetween.

15. The disposable undergarment of claim 14, wherein said waist-opening of said pants is seamlessly connected to said lower opening of said belly protector along an imaginary boundary line; and said-liquid absorbent core does not extend beyond the imaginary boundary line and stops at a distance therefrom.

* * * * *